United States Patent [19]

Shakkottai et al.

[11] Patent Number: 5,211,052
[45] Date of Patent: May 18, 1993

[54] AEROACOUSTIC GAS COMPOSITION MONITOR

[75] Inventors: Parthasarathy Shakkottai, Duarte; Eug Y. Kwack, Walnut, both of Calif.

[73] Assignee: Sparktech, Duarte, Calif.

[21] Appl. No.: 598,017

[22] Filed: Oct. 11, 1990

[51] Int. Cl.⁵ .......................................... G01N 37/00
[52] U.S. Cl. ..................... 73/23.2; 73/31.05
[58] Field of Search .......... 73/23.35, 23.36, 23.37, 73/23.39, 23.4, 24.01, 24.05, 24.06, 30.01, 30.04, 31.01, 31.02, 31.03, 31.04, 31.05, 861.27, 861.28, 861.18, 23.2; 374/117, 118

[56] References Cited

U.S. PATENT DOCUMENTS 4,896,540  1/1990  Shakkottai .................. 73/861.02

OTHER PUBLICATIONS

Shakkottai et al., "High Intensity Tone Generation by Aeroacoustic Sources", J. Acoust. Soc. Am, 82, (6), Dec. 1987, pp. 2075-2085.

Shakkottai, et al., "Tone Generation By Aeroacoustic Sources in Pipes with Flow" J. Acoust. Soc. AM, 87(4), Apr. 1990, pp. 1489-1496.

Primary Examiner—Hezron E. Williams
Assistant Examiner—Michael J. Brock

[57] ABSTRACT

The composition monitor uses a flow driven acoustic resonator whose frequency is simply related to the speed of sound of the gaseous mixture present in the cavity resonator. Because the speed of sound is a function of temperature and composition of mixtures, the oscillator frequency signal may be used to measure the composition and control the process. The aeroacoustic sources have the advantage that they are immune to high pressure and high temperature and are energized by flows leading into or out of reactors. In addition, sound is led to a measurement microphone from the source by a solid rod which isolates it from high pressure and temperature obtaining thereby a robust sensor.

6 Claims, 4 Drawing Sheets

AEROACOUSTIC GAS COMPOSITION MONITOR

BACKGROUND OF THE INVENTION

1. Field of the Invention

The present invention is directed to a device and method of deriving the composition of a mixture of a few gases such as are found in chemical cracking processes etc., by determining the frequency of oscillation of an aeroacoustic whistle source driven by the flow itself.

2. Description of the prior Art

Composition of a mixture of gases is commonly determined by gas chromatograph-mass spectrometers. These instruments are not convenient for on-line process control even though they do work very well in analytical laboratories. Process control mass spectrometers are also coming into use where many gases in mixtures can be sampled and analyzed rapidly. For example, the Milton Roy on-line MS system can analyze 32 components per sample location 20 seconds [1]. Many sample streams are brought to a single location to be sampled by a single mass spectrometer. However, the task of bringing many samples to one location in a large chemical plant is not a simple one.

Gas chromatographs can also be used instead of mass-spectrometers for monitoring the composition of mixtures. An analysis can be done in a few minutes. However, the problem associated with gas sampling remain.

OBJECTS AND SUMMARY OF THE INVENTION

It is a primary object of the present invention to provide a device for monitoring the composition of a mixture of gases by a measurement of the speed of sound through the mixture which depends on the relative proportions of the various gases in the mixture. The speed of sound is determined by measuring the frequency of an aeroacoustic whistle, either of the ring cavity type with the cavity formed in the wall of a pipe or, if it is inconveniently large, a smaller unit that can be inserted into a process stream.

BRIEF DESCRIPTION OF THE DRAWINGS

A more complete appreciation of the invention and the attendant advantages thereof will be more clearly understood by reference to the following drawings herein.

DESCRIPTION OF THE PREFERRED EMBODIMENTS

Introduction

Figure 1:
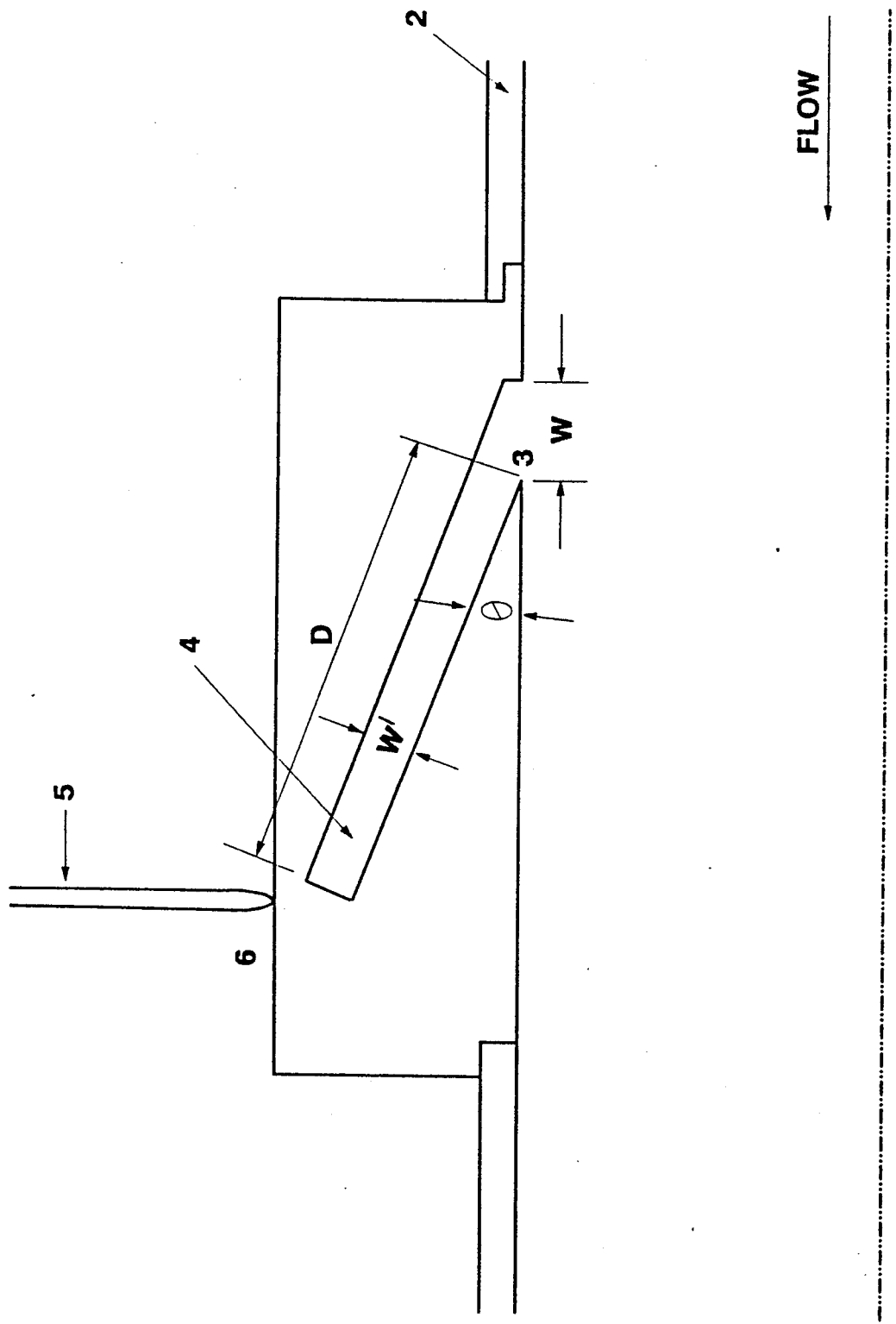
FIG. 1 shows a cross section of an aeroacoustic whistle consisting of a conical cavity and a sharp edge which is set into acoustic resonant oscillations by the internal flow in the pipe.

For a pure gas, it is well known that the speed of sound is given by $$c = (\gamma kT/m)^{\frac{1}{2}}, \quad (1)$$

which depends on the ratio of specific heats $\gamma$, temperature T and the mass of a molecule, m. Here k denotes the Boltzmann constant. A measurement of c and T is usually sufficient to determine m because $\gamma$ does not vary very much and has the value 4/3 for all polyatomic gases with 6 degrees of freedom. More accurate values of $\gamma$ at different temperatures are either available from suitable chemical tables or can be obtained experimentally.

$$c^2 = kT(1 + 2/f_a)/m_2, \quad (2)$$

where the mean mass is given in terms of number densities $n_i$ of species i by $$m_a = \Sigma m_i n_i / \Sigma n_i, \quad (3)$$

and the mean number of degrees of freedom $$f_a \Sigma f_i n_i / \Sigma n_i. \quad (4)$$

Application for Process Control

The usefulness of a measurement of the speed of sound for process control is illustrated by two examples.

EXAMPLE 1

Consider the process of conversion of benzene to cyclohexane by the addition of hydrogen, represented by the reaction $$C_6H_6 + 3H_2 \rightarrow C_6H \quad (5)$$

At the output of a reactor, the number densities of $C_6H_6$, $H_2$ and $C_6H_{12}$ will be proportional to $(1-\beta), (3-3\beta)$ and if $\beta$ represents the fraction converted. The masses are proportional to 78, 2 and 84 respectively (the respective molecular weights) and the values of f are 6, 5 and 6 because $H_2$ has 5 degrees of freedom. The mixture is therefore characterized by $$m_a 84 m_H/(4-3\beta), \quad (6)$$

and $$f_a (21-5\beta)/(4-3\beta), \quad (7)$$

where $m_H$ is the mass of a hydrogen atom. Using (5) and (6) in (1), $$m_H c^2/kT = (4-3\beta)(29-21\beta)/(84(21-15\beta)). \quad (8)$$

It is clear that $c^2$ in (8) is a strong function of $\beta$ as the following short table shows:

TABLE

| $\beta$ | 0 | 0.25 | 0.5 | 0.75 | 1.0 |

| TABLE-continued | | | | | |
|---|---|---|---|---|---|
| $84m_Hc^2/kT$ | 5.52 | 4.10 | 3.42 | 2.38 | 1.33 |

This example shows that by a measurement of c or $c^2\beta$ can be measured and used as a control variable in process control.

EXAMPLE 2

In the first example there were only 3 gases in the mixture. In this second, there are more. This is the hydrocarbon cracking process starting from butane where we can assume the following reaction for illustration [2]

$$4C_4H_{10} \rightarrow C_4H_8 + C_4H_6 + C_3H_6 + C_2H_6 + 3CH_4 + H_2 \quad (9)$$

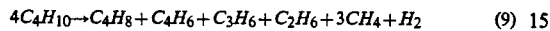

| m/m$_H$ | 58 | 56 | 54 | 42 | 30 | 16 | 2 |
|---|---|---|---|---|---|---|---|
| n | 4(1 − β) | β | β | β | β | 3β | β |
| f | 6 | 6 | 6 | 6 | 6 | 6 | 5 |

Using (2) and (3), for this case, $$m_a = 58/(1+\beta) \quad (10)$$

$$f_a = (24 + 23\beta)/(4 + 4\beta). \quad (11)$$

From (1), $$58c^2 m_H/kT = (1+\beta)(32 + 31\beta)/(24 + 23\beta). \quad (12)$$

The following table shows the calculated dependence of $c^2$ on $\beta$.

TABLE

| β | 0 | 0.25 | 0.5 | 0.75 | 1.0 |
|---|---|---|---|---|---|
| $58m_Hc^2/kT$ | 1.33 | 1.67 | 2.01 | 2.34 | 2.68 |

This again shows that β may be determined from $c^2$ with excellent resolution. Whenever a reaction produces light gases such as $CH_4$ and $H_2$, the speed of sound increases and this may be put to good use in process control.

Measurement of the Speed of Sound

Sound speed may be measured by time-of-flight methods or by a measurement of frequency of a resonant cavity which contains the gas of interest. The most convenient for use in a moving flow would be to use a cavity oscillator driven by the flow itself.

In U.S. Pat. No. 4,896,540, Shakkottai and Kwack describe the use of aeroacoustic ring cavities for the generation of plane waves of sound in a pipe together with a phase measurement method to determine the average rate of flow of the gas [3]. A simpler system where the ring cavity is merely used to generate sound of a frequency that is related to the speed of sound is adequate for process control.

The behavior of internal ring cavities have been described in the patent above. A more recent paper on tone generation by aeroacoustic sources in pipes with flow by Shakkottai et. al. in J. Acoustic Society. Am 87(4), Apr. 1990, pp 1489-1496, gives further details [4]. Ring cavity sources external to a body such as a round nosed projectile is described in earlier papers by Shakkottai et. al. in "High Intensity Tone Generation by Aeroacoustic Sources", J. Acoust. Society Am 82(6), December 87, pp 2075-2085 [5]. The relation between frequency and cavity dimensions is the most important characteristic for the application of an aeroacoustic sensor for process control.

For internal cavities, i.e. cavities in internal flow as shown in FIG. 1, the speed of sound is given by $$c = 4(1 - M^2)D_e f, \quad (13)$$

where $D_e$ is an effective depth of the ring cavity, f is the frequency of the oscillation and M is the flow Mach number. The correction $(1 - M^2)$ is usually quite small but can be taken into account, if necessary.

Figure 2:
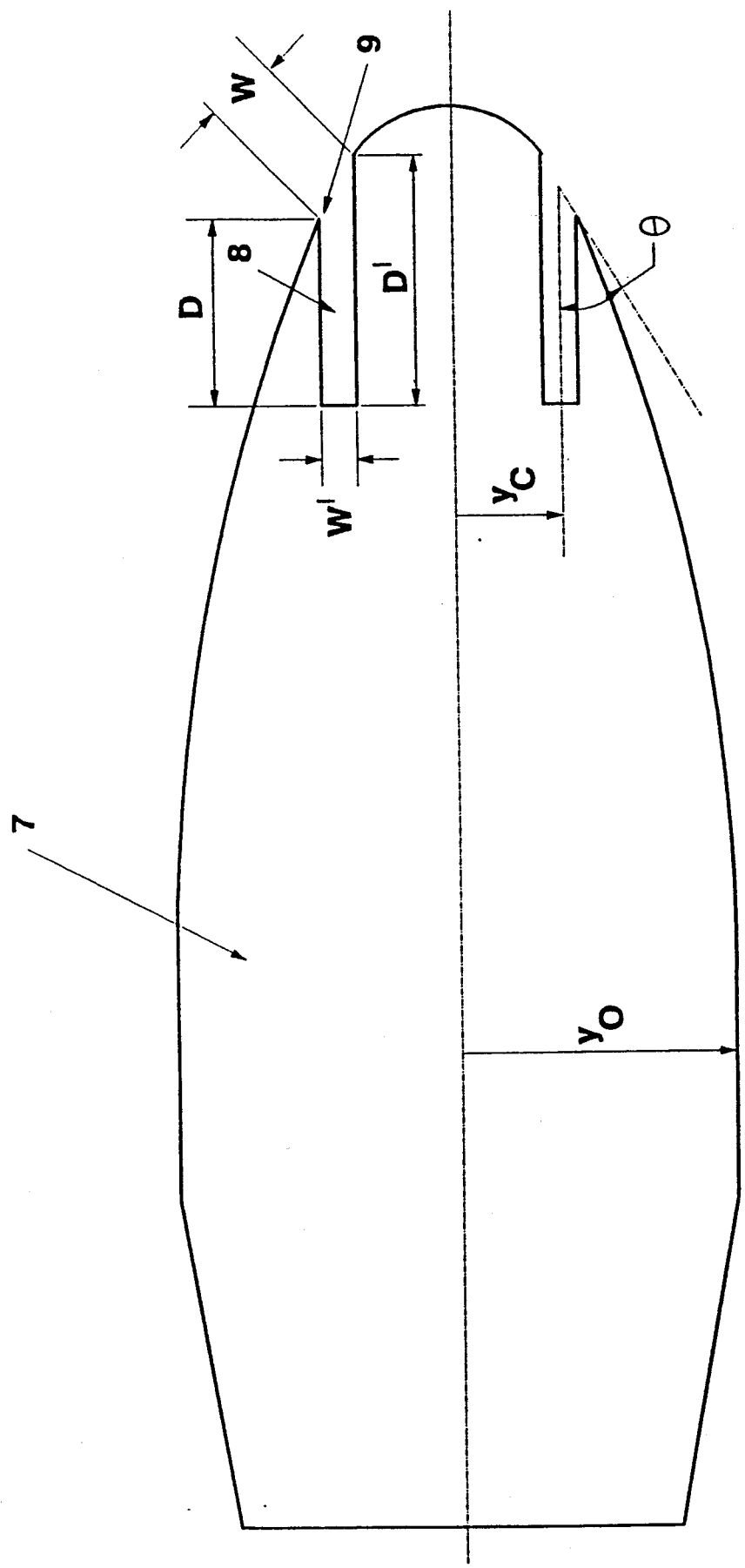
FIG. 2 shows a cross section of an aeroacoustic ring cavity formed by machining out an axisymmetric cavity in a round nosed body. The external flow moving past the sharp edge creates flow oscillations which drive the cavity into acoustic resonance.

For external ring cavities such as on round nosed bodies as shown in FIG. 2.

$$c = 4D_e f, \quad (14)$$

where $D_e$ is the effective depth.

An aeroacoustic whistle containing an internal ring cavity may be used in pipe sizes up to several inches diameter, say 10, after which the device is very big in size and also generates an unnecessarily large intensity of sound. For large sizes a smaller round nosed body containing an external ring cavity is more economical.

Internal ring cavity source

Flow 1 through the pipe 2 moves past the gap of width w and is made unstable by the sharp edge 3 which generates vortices periodically. Pressure disturbances sustain themselves at a frequency selected by the resonant cavity 4 which is conical and has a depth D. The effective depth $D_e$ is slightly larger because of an end correction common to all organ pipes. The average depth $D_a$ which is defined by the projected area of the cavity divided by the width w' together with $\alpha w'$ is the effective length. The factor $\alpha$ is the Rayleigh end correction and has the value $4/3\pi$. At resonance, $D_a + \alpha w' = 4\lambda$, where $\lambda$ is the wavelength of sound. Sound can be detected by a solid probe touching a point 6 on the outside of the piping system near the bottom of the cavity as shown, where the intensity of pressure fluctuations is the strongest.

The flow range over which a ring source operates is wide. For example, in a pipe of 12.7 cm i.d., the cavity is excited over the flow range 40 m/s to 140 m/s for a gap=0.89 cm. There is one peculiarity in this case which makes it possible for oscillation to occur at another pipe mode with $$fD_e(1 - M^2)/c = 0.345. \quad (16)$$

For a process control application, the frequency jump must be recognized when it occurs.

One way of increasing the flow range over which the oscillation occur is to use two (or more) ring sources separated by a half wavelength which is also equal to double the effective cavity depth. The first may be set to oscillate from 30 to 70 m/s and the second from 40 m/s to 140 m/s. The contribution is expected to operate over a range exceeding 30 to 140 m/s because of mutual reinforcement.

External Ring Cavity Source

By machining out material from a round nosed body 7, an axisymmetric ring cavity 8 with a sharp edge 9 is formed. The geometrical characteristics are described by radius $y_o$, location of the cavity center radius $y_c$, width w', depth D and D', gap w, slope at the cavity location θ. The effective depth is given by the mean depth $(D+D')/2$ plus the Rayleigh correction $\alpha w'$. This can be shown to be equal to $$D_e D + (\cos\theta/2 + \alpha\sin\theta)w. \quad (17)$$

The frequency of oscillation is given by dividing the speed of sound c by $4D_e$.

The axisymmetric ring cavity generates sound aerodynamically, such that the parameters w and $\theta$ determine the velocity range over which oscillations occur and the depth $D_e$ determines frequency. A convenient size of whistle has a diameter of 4.7 cm. A good whistle has the following dimensions $D = 1.78$ cm $w' = 0.152$ cm $y_c 32\ 1.83$ cm In ambient air this source whistles at 4000 Hz, in the fundamental mode between 35 m/s to 130 m/s. The dynamic pressure correspondingly ranges between $\frac{1}{2}(35)^2$ Nm$^{-2}$ to $\frac{1}{2}(130)^2$ Nm$^{-2}$. This shows that for heavier gasses the whistle operates over lower speeds. For example a gas that is five times denser than air flowing at a pressure of 10 atmospheres will excite the whistle over a speed range which is $(50)^{\frac{1}{2}}$ times smaller. In the above case, the range could be from 4.94 m/s to 18.4 m/s. This example shows that the above whistle would operate successfully in most processes. Whistles for other ranges can be designed using the information in the reference mentioned earlier.

Whistles for Extremely Low Flows

Figure 3:
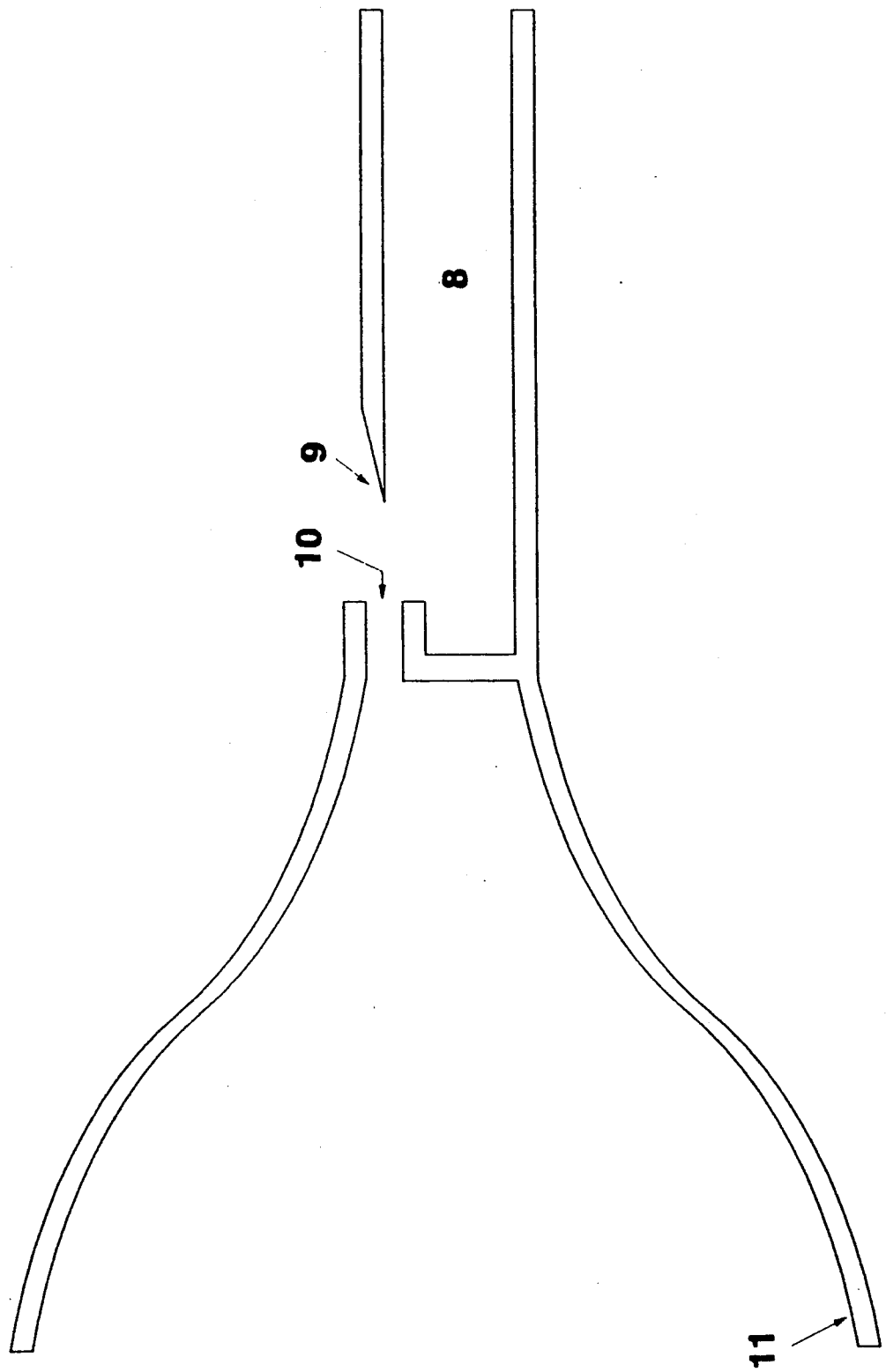
FIG. 3 is a cross section of a small organ pipe which operates at very low flow rates. The bell mouth captures a certain amount of flow and forces this to go past a sharp edged cavity as in all aeroacoustic whistles. The cavity may be open or closed at the far end. In this figure it is shown open.

Flue pipes oscillate with extremely low velocity flow excitation (in the range of 0.1 to 0.3 m/s in ambient air) and can be used inside reaction vessels where velocities may be orders of magnitude lower than at the inlet and outlet. Normally in large reactors it is not desirable to introduce a device that requires a long support etc. but there may be cases where it would be tolerated. The whistle for this purpose would resemble an organ pipe and is shown in FIG. 3.

The pipe with a cavity 8 and a sharp edge 9 over a part of its circumference which may be flattened is excited by the flow through the gap 10. The bell mouth 11 captures an amount of flow to form the jet required to play against edge 9.

Detection of Sound

Figure 4:
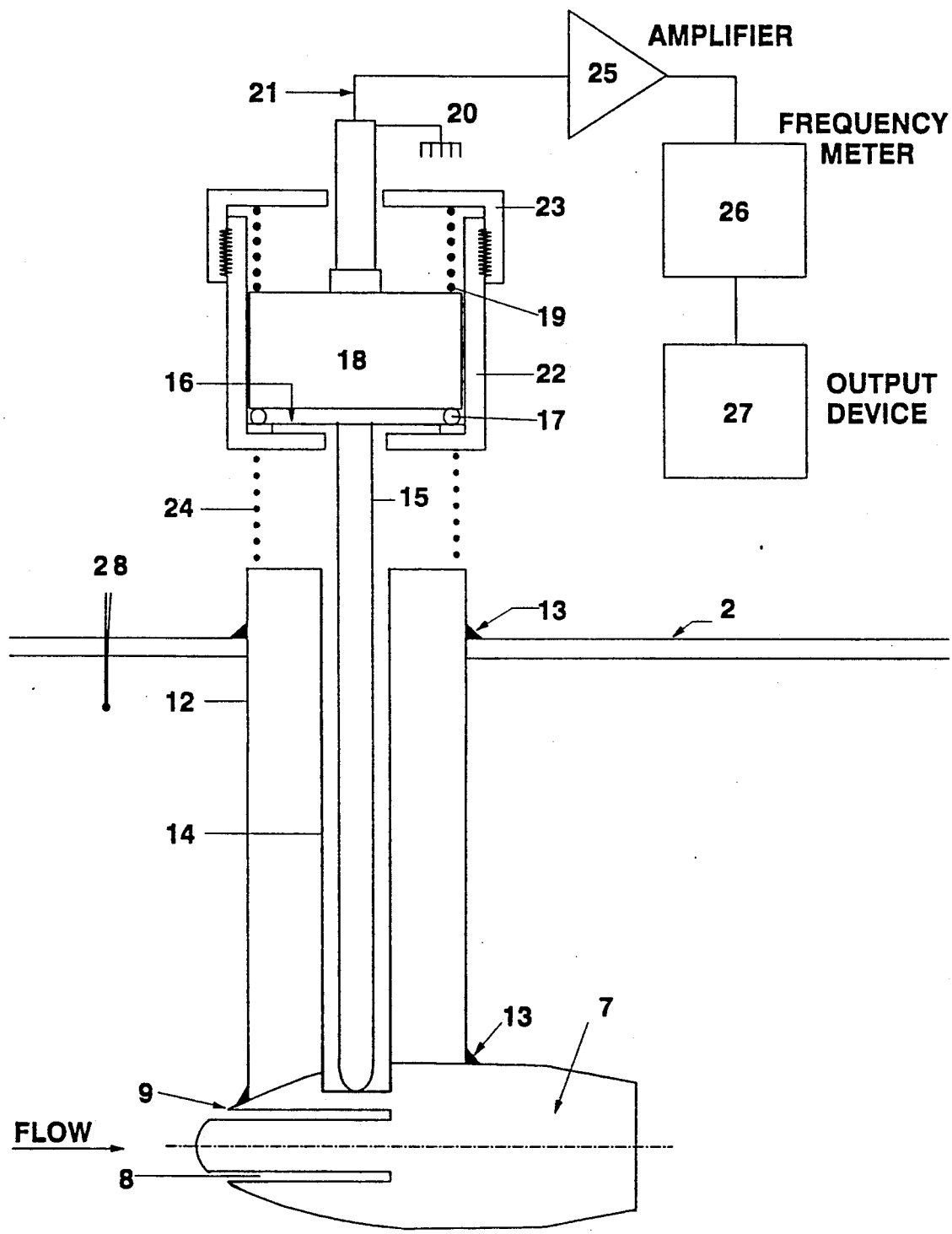
FIG. 4 shows an aeroacoustic ring cavity of the external flow type installed in a large pipe. Acoustic oscillations are conducted by a solid rod to a diaphragm, and to air in a gap above which a microphone is mounted to detect the oscillations. The long rod of stainless steel allows poor heat conduction from the hot gas. The microphone is uncooled.

For use in corrosive, hot, high-pressure media, it is necessary for the sound detection microphone not to come in contact with the gas. Because we are only interested in the frequency of oscillation but not its spatial variation and its phase change, it is possible to lead the sound to the microphone through a solid rod as shown in FIG. 4 which shows a complete installation using a ring source 7 for external flow with ring cavity 8 and sharp edge 9. A stainless steel bracket 12 is welded at 13 to ring source 7 and pipe 2. The cross section of bracket 12 is oval to minimize drag. A drilled hole 14 allows the solid probe 15 to sense vibration at a point close to the bottom of the ring cavity 8 and communicate it through diaphragm 16 to air above it. Microphone 18 separated by O-ring 17 with diaphragm 16 senses these vibrations. Tension springs 24 keep the probe pressed lightly on to source 7. Springs 19 hold microphone 18 snugly within housing 22 with lid 23.

The signal comes out through a coaxial cable with signal lead 21 and grounded outer shield 20. The signal is amplified by amplifier 25 whose output is fed to frequency meter 26. The measured frequency is used by the output device 27 which can be a microcomputer with many control outputs, alarm etc., to control the process. A thermocouple 28 provides the temperature signal to the output device 27 because it is also needed in the calculation of composition.

Summary and Conclusions

It is possible to measure the speed of sound of gaseous mixtures by using flow driven acoustically resonant cavity oscillators whose frequency is proportional to the speed of sound in the case of unconfined flows. In the case of sources confined within the reverberant environment of pipes, an additional small factor $(1-M^2)$ also enters in the equation. Three types of oscillators can be used: (1) cavity oscillators operated by external flow as on a round nosed body or (2) by internal flow as in the case of flow grazing past the circumference of a pipe where conical cavity source is located or (3) by small organ pipes with flow catchers in the case of very small velocities. Because the source operates at high temperatures and high pressures, solid borne sound is conducted to the measurement location where the frequency signal is sensed by an uncooled microphone. Because the relation between the frequency and gas composition can be easily established for each reaction, the signal can be used for process control. Samples of hydrogenation and cracking reactions show the sensitivity of the method which is passive. The sensor is very robust.

REFERENCES

1. "PRO SPEC 2000 Process Mass Spectrometer, Milton Roy Brochure 2-89, Process Analytical Division", 1220-c Simon Circle, Anaheim, Calif. 92806.

2. Soudek and Lacatena, "Crack Isobutane for Isobutylene" Hydrocarbon Processing, Vol. 69, 5, May 1990, pp. 73-76.

3. Shakkottai and Kwack, U.S. Pat. No. 4,896,540, Jan. 30, 1990, "Aeroacoustic Flowmeter."

4. Shakkottai, et al, "Tone Generation by Aeroacoustic Sources in Pipes with Flow," J. Acoust. Soc. Am., 87 (4), Apr. 1990, pp. 1489-1496.

5. Shakkottai, et al., "High-intensity tone generation by aeroacoustic sources," J. Acoust. Soc. Am., 82 (6), Dec. 1987, pp. 2075-2085.

We claim:

1. A system for processing signals and deriving the mole fraction of a chosen gas in a mixture of gases flowing in a large pipe, the arrangement comprising:

an aeroacoustic ring source located on a round nosed body installed at the center of said pipe, said source containing a sharp edge and a ring cavity producing periodic oscillations in said cavity, said oscillations being generated by said flow; means to isolate heat and pressure at said ring source and to conduct solid-borne sound from the back of said cavity to a diaphragm, in the form of a poorly heat conducting rod, said rod being located within a long drilled hole within a support sting welded to said ring source; said diaphragm enclosing a small volume of air within which an uncooled microphone is mounted to sense air-borne pressure fluctuations generated in said volume of air by said diaphragm vibrating in response to said solid-borne sound; an arrangement of springs to keep said rod pressed lightly to said ring source; electronic amplifying means to amplify signals from said microphone; a frequency meter or counter to measure frequencies of said signals; thermocouple means for measuring the average temperature of said mixture of gases; output means for calculating and displaying the desired temperature, speed of sound and mole fraction for use as control signals for process control.

2. A system as described in claim 1 wherein the cavity depth of said ring cavity ranges from approximately 2 cm to 10 cm corresponding to frequencies in air at 300 K ranging from 4375 Hz to 875 Hz, for convenient measurements in pipes of large diameter said ring source being located on a round nosed body of diameter in the range 3 cm to 8 cm.

3. A system for processing signals and deriving the mole fraction of a chosen gas in a mixture of gases flowing in a pipe, the arrangement comprising:

non-obstructing aeroacoustic ring source located on the circumference of said pipe, said source containing a sharp edge and a ring cavity producing periodic oscillations in said cavity, said oscillations being generated by said flow; means to isolate heat and pressure at said ring source and to conduct solid-borne sound from the back of said cavity to a diaphragm, in the form of a poorly heat conducting rod, said rod being located within a long drilled hole within a support sting welded to said ring source; said diaphragm enclosing a small volume of air within which an uncooled microphone is mounted to sense air-borne pressure fluctuations generated in said volume of air by said diaphragm vibrating in response to said solid-borne sound; an arrangement of springs to keep said rod pressed lightly to said ring source; electronic amplifying means to amplify signals from said microphone; a frequency meter or counter to measure frequencies of said signals; thermocouple means for measuring the average temperature of said mixture of gases; output means for calculating and displaying the desired temperature, speed of sound and mole fraction for use as control signals for process control.

4. A system described in claim 3 wherein said ring cavity depth ranges from approximately 2 cm to 10 cm corresponding to frequencies in air at 300 K ranging from 4375 Hz to 875 Hz, for convenient measurements in pipes of diameters below approximately 10 in.

5. A system for processing signals and deriving the mole fraction of a chosen gas in a mixture of gases in a reactor, the arrangement comprising:

an aeroacoustic source suitable for use at extremely low flow speeds inside said reactor taking the form of a small organ pipe with a flow collector, said source containing a sharp edge and a cavity in the form of said organ pipe, producing periodic oscillations in said cavity, said oscillations being generated by said flow; means to isolate heat and pressure at said source and to conduct solid-borne sound from the middle of said cavity to a diaphragm, in the form of a poorly heat conducting rod, said rod being located within a long drilled hole within a support sting welded to said ring source; said diaphragm enclosing a small volume of air within which an uncooled microphone is mounted to sense air-borne pressure fluctuations generated in said volume of air by said diaphragm vibrating in response to said solid-borne sound; an arrangement of springs to keep said rod pressed lightly to said organ pipe; electronic amplifying means to amplify signals from said microphone; a frequency meter or counter to measure frequencies of said signals; thermocouple means for measuring the average temperature of said mixture of gases; output means for calculating and displaying the desired temperature, speed of sound and mole fraction for use as control signals for process control.

6. A system as described in claim 5 wherein the length of said organ pipe ranges from approximately 10 cm to 40 cm corresponding to frequencies in air at 300 K ranging from 1750 Hz to 437 Hz, for convenient measurements in said reactor, the diameter of said organ pipe being in the range 5 mm to 30 mm.

* * * * *